United States Patent
Zhu et al.

(10) Patent No.: US 10,420,938 B2
(45) Date of Patent: *Sep. 24, 2019

(54) SYSTEMS AND METHODS FOR DELIVERING THERAPY TO THE DORSAL HORN OF A PATIENT

(71) Applicant: Boston Scientific Neuromodulation Corporation, Valencia, CA (US)

(72) Inventors: Changfang Zhu, Valencia, CA (US); Michael A. Moffitt, Saugus, CA (US); Bradley Lawrence Hershey, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/985,165

(22) Filed: May 21, 2018

(65) Prior Publication Data

US 2018/0264267 A1  Sep. 20, 2018

Related U.S. Application Data

(63) Continuation of application No. 14/556,742, filed on Dec. 1, 2014, now Pat. No. 10,010,715.

(Continued)

(51) Int. Cl.
*A61N 1/36* (2006.01)
*A61N 1/05* (2006.01)
*A61N 1/372* (2006.01)

(52) U.S. Cl.
CPC ..... *A61N 1/36071* (2013.01); *A61N 1/36182* (2013.01); *A61N 1/0551* (2013.01); *A61N 1/36185* (2013.01); *A61N 1/37247* (2013.01)

(58) Field of Classification Search
CPC .......... A61N 1/36071; A61N 1/36182; A61N 1/37247; A61N 1/0551; A61N 1/36185
See application file for complete search history.

(56) References Cited

U.S. PATENT DOCUMENTS

| | | |
|---|---|---|
| 5,938,690 A | 8/1999 | Law et al. |
| 5,941,906 A | 8/1999 | Barreras, Sr. et al. |

(Continued)

FOREIGN PATENT DOCUMENTS

| | | |
|---|---|---|
| WO | WO-2006029257 A2 | 3/2006 |
| WO | WO-2006135791 A2 | 12/2006 |

OTHER PUBLICATIONS

"U.S. Appl. No. 14/556,742, Final Office Action dated May 9, 2017", 7 pgs.

(Continued)

*Primary Examiner* — Catherine M Voorhees
*Assistant Examiner* — Roland Dinga
(74) *Attorney, Agent, or Firm* — Schwegman Lundberg & Woessner, P.A.

(57) ABSTRACT

A method of operating an implantable neuromodulator coupled to an electrode array implanted adjacent tissue of a patient having a medical condition comprises conveying electrical modulation energy to tissue of the patient in accordance with a modulation parameter set, wherein conveying the electrical modulation energy to tissue of the patient in accordance with the modulation parameter set stimulates dorsal horn neuronal elements more than dorsal column neuronal elements.

20 Claims, 8 Drawing Sheets

Related U.S. Application Data

(60) Provisional application No. 61/911,728, filed on Dec. 4, 2013.

(56) References Cited

U.S. PATENT DOCUMENTS

| | | |
|---|---|---|
| 6,516,227 B1 | 2/2003 | Meadows et al. |
| 6,675,046 B2 | 1/2004 | Holsheimer |
| 6,895,280 B2 | 5/2005 | Meadows et al. |
| 6,993,384 B2 | 1/2006 | Bradley et al. |
| 7,317,948 B1 | 1/2008 | King et al. |
| 7,333,857 B2 | 2/2008 | Campbell |
| 7,539,538 B2 | 5/2009 | Parramon et al. |
| 7,613,519 B2 | 11/2009 | De Ridder |
| 7,627,384 B2 | 12/2009 | Ayal et al. |
| 7,650,184 B2 | 1/2010 | Walter |
| 7,979,133 B2 | 7/2011 | Feler et al. |
| 7,987,000 B2 | 7/2011 | Moffitt et al. |
| 8,019,439 B2 | 9/2011 | Kuzma et al. |
| 8,160,328 B2 | 4/2012 | Goetz et al. |
| 8,180,129 B2 | 5/2012 | Goetz et al. |
| 8,224,453 B2 | 7/2012 | De Ridder |
| 8,255,057 B2 | 8/2012 | Fang et al. |
| 8,355,797 B2 | 1/2013 | Caparso et al. |
| 8,380,318 B2 | 2/2013 | Kishawi et al. |
| 8,412,345 B2 | 4/2013 | Moffitt |
| 8,437,857 B2 | 5/2013 | Moffitt et al. |
| 8,455,716 B2 | 6/2013 | Huang et al. |
| 8,504,147 B2 | 8/2013 | Deem et al. |
| 8,615,300 B2 | 12/2013 | Feler et al. |
| 8,649,874 B2 | 2/2014 | Alataris et al. |
| 8,660,653 B2 | 2/2014 | Kothandaraman |
| 8,670,831 B2 | 3/2014 | Wacnik et al. |
| 8,676,329 B2 | 3/2014 | Wacnik et al. |
| 8,676,331 B2 | 3/2014 | Parker |
| 8,700,178 B2 | 4/2014 | Anderson |
| 8,731,675 B2 | 5/2014 | Ranu et al. |
| 8,751,009 B2 | 6/2014 | Wacnik |
| 10,010,715 B2 * | 7/2018 | Zhu ................ A61N 1/36071 |
| 2003/0139781 A1 | 7/2003 | Bradley et al. |
| 2004/0116978 A1 | 6/2004 | Bradley |
| 2007/0150036 A1 | 6/2007 | Anderson |
| 2008/0188909 A1 | 8/2008 | Bradley |
| 2009/0196472 A1 | 8/2009 | Goetz et al. |
| 2009/0198306 A1 | 8/2009 | Goetz et al. |
| 2009/0204173 A1 | 8/2009 | Fang et al. |
| 2009/0270960 A1 | 10/2009 | Zhao et al. |
| 2010/0010566 A1 | 1/2010 | Thacker et al. |
| 2010/0121409 A1 | 5/2010 | Kothandaraman et al. |
| 2010/0249875 A1 | 9/2010 | Kishawi et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274317 A1 | 10/2010 | Parker et al. |
| 2010/0274318 A1 | 10/2010 | Walker et al. |
| 2010/0274326 A1 | 10/2010 | Chitre et al. |
| 2011/0282414 A1 | 11/2011 | Kothandaraman et al. |
| 2012/0059446 A1 | 3/2012 | Wallace et al. |
| 2012/0083709 A1 | 4/2012 | Parker et al. |
| 2012/0089200 A1 | 4/2012 | Ranu et al. |
| 2012/0253422 A1 | 10/2012 | Thacker et al. |
| 2012/0265279 A1 | 10/2012 | Zhu et al. |
| 2012/0283797 A1 | 11/2012 | De Ridder |
| 2012/0290041 A1 | 11/2012 | Kim et al. |
| 2013/0066411 A1 | 3/2013 | Thacker et al. |
| 2013/0096643 A1 * | 4/2013 | Fang ................ A61N 1/36071 607/46 |
| 2013/0116752 A1 | 5/2013 | Parker et al. |
| 2013/0268021 A1 | 10/2013 | Moffitt |
| 2013/0296975 A1 | 11/2013 | Lee et al. |
| 2014/0081349 A1 | 3/2014 | Lee et al. |
| 2014/0277267 A1 | 9/2014 | Vansickle et al. |
| 2015/0151125 A1 | 6/2015 | Zhu et al. |

OTHER PUBLICATIONS

"U.S. Appl. No. 14/556,742, Non Final Office Action dated Sep. 5, 2017", 11 pgs.

"U.S. Appl. No. 14/556,742, Non Final Office Action dated Sep. 29, 2016", 12 pgs.

"U.S. Appl. No. 14/556,742, Notice of Allowance dated Mar. 7, 2018", 8 pgs.

"U.S. Appl. No. 14/556,742, Response filed Jan. 6, 2017 to Non Final Office Action dated Sep. 29, 2016", 14 pgs.

"U.S. Appl. No. 14/556,742, Response filed Jun. 27, 2017 to Final Office Action dated May 9, 2017", 8 pgs.

"U.S. Appl. No. 14/556,742, Response filed Nov. 27, 2017 to Non Final Office Action dated Sep. 5, 2017", 9 pgs.

Kothandaraman, Sridhar, et al., "System and Method for Connecting Devices to a Neurostimulator", U.S. Appl. No. 61/694,695, filed Aug. 29, 2012.

Lee, Dongchul, "Neurostimulation System for Defining a Generalized Ideal Multipole Configuration", U.S. Appl. No. 61/452,965, filed Mar. 15, 2011.

Rao, Prakash, et al., "Technique for Linking Electrodes Together During Programming of Neurostimulation System", U.S. Appl. No. 61/561,760, filed Nov. 18, 2011.

Vansickle, Dennis Allen, et al., "Neuromodulation System and Method for Transitioning Between Programming Modes", U.S. Appl. No. 14/214,752, filed Mar. 15, 2014.

Vansickle, Dennis Allen, "Systems and Methods for Delivering Sub-Threshold Therapy to a Patient", U.S. Appl. No. 61/801,917, filed Mar. 15, 2013.

Warman, Eduardo N., et al., "Modeling the Effects of Electric Fields on Nerve Fibers: Determination of Excitation Thresholds", IEEE Transactions on Biomedical Engineering, vol. 39, No. 12, Dec. 1992, (Dec. 1992).

Zhu, Changfang, et al., "Neurostimulation System for Estimating Desired Stimulation Amplitude for Electrode Configuration", U.S. Appl. No. 61/427,027, filed Dec. 23, 2010.

Zhu, Changfang, et al., "Neurostimulation System for Implementing Model-Based Estimate of Neurostimulation Effects", U.S. Appl. No. 61/427,059, filed Dec. 23, 2010.

* cited by examiner

_SYSTEMS AND METHODS FOR DELIVERING THERAPY TO THE DORSAL HORN OF A PATIENT_

CLAIM OF PRIORITY

This application is a continuation of U.S. application Ser. No. 14/556,742, filed Dec. 1, 2014, which claims the benefit of priority under 35 U.S.C. § 119(e) of U.S. Provisional Patent Application Ser. No. 61/911,728, filed on Dec. 4, 2013, each of which is herein incorporated by reference in its entirety.

FIELD OF THE INVENTION

The present inventions relate to tissue modulation systems, and more particularly, to programmable neuromodulation systems.

BACKGROUND OF THE INVENTION

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neuromodulation systems typically include one or more electrodes carrying stimulation leads, which are implanted at the desired stimulation site, and an implantable neuromodulation device (e.g., an implantable pulse generator (IPG)) implanted remotely from the stimulation site, but coupled either directly to the neuromodulation lead(s) or indirectly to the neuromodulation lead(s) via a lead extension. The neuromodulation system may further comprise a handheld external control device (e.g., a remote control (RC)) to remotely instruct the neuromodulator to generate electrical stimulation pulses in accordance with selected modulation parameters.

Implantable neuromodulation devices are active devices requiring energy for operation, and thus, the neuromodulation system oftentimes includes an external charger to recharge a neuromodulation device, so that a surgical procedure to replace a power depleted neuromodulation device can be avoided. To wirelessly convey energy between the external charger and the implanted neuromodulation device, the charger typically includes an alternating current (AC) charging coil that supplies energy to a similar charging coil located in or on the neuromodulation device. The energy received by the charging coil located on the neuromodulation device can then be stored in a rechargeable battery within the neuromodulation device, which can then be used to power the electronic componentry on-demand. Depending on the settings, the neuromodulation device may need to be recharged every 1-30 days.

Electrical stimulation energy may be delivered from the neuromodulation device to the electrodes in the form of an electrical pulsed waveform. Thus, stimulation energy may be controllably delivered to the electrodes to stimulate neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses provided through the electrode array. Each electrode configuration, along with the electrical pulse parameters, can be referred to as a "modulation parameter set."

The lead or leads are typically placed in a location, such that the electrical stimulation will cause paresthesia. The current understanding is that paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When electrical leads are implanted within the patient, the computerized programming system, in the context of an operating room (OR) mapping procedure, may be used to instruct the neuromodulation device to apply electrical stimulation to test placement of the leads and/or electrodes, thereby assuring that the leads and/or electrodes are implanted in effective locations within the patient.

Although alternative or artifactual sensations are usually appreciated by patients, patients sometimes report these sensations to be uncomfortable, and therefore, they can be considered an adverse side-effect to neuromodulation therapy in some cases. It has been shown that the delivery of sub-threshold electrical energy (e.g., high-rate pulsed electrical energy and/or low pulse width electrical energy) can be effective in providing neuromodulation therapy for chronic pain without causing paresthesia.

Once the leads are correctly positioned, a fitting procedure, which may be referred to as a navigation session, may be performed using the computerized programming system to program the external control device, and if applicable the neuromodulation device, with a set of modulation parameters that best addresses the painful site. Thus, the navigation session may be used to pinpoint the volume of activation (VOA) or areas correlating to the pain. Such programming ability is particularly advantageous for targeting the tissue during implantation, or after implantation should the leads gradually or unexpectedly move that would otherwise relocate the stimulation energy away from the target site. By reprogramming the neuromodulation device (typically by independently varying the stimulation energy on the electrodes), the volume of activation (VOA) can often be moved back to the effective pain site without having to re-operate on the patient in order to reposition the lead and its electrode array. When adjusting the volume of activation (VOA) relative to the tissue, it is desirable to make small changes in the proportions of current, so that changes in the spatial recruitment of nerve fibers will be perceived by the patient as being smooth and continuous and to have incremental targeting capability.

An external control device can be used to instruct the neuromodulation device to generate electrical stimulation pulses in accordance with the selected modulation parameters. Typically, the modulation parameters programmed into the neuromodulation device can be adjusted by manipulating controls on the external control device to modify the electrical stimulation provided by the neuromodulation device system to the patient. Thus, in accordance with the modulation parameters programmed by the external control device, electrical pulses can be delivered from the neuromodulation device to the stimulation electrode(s) to stimulate or activate a volume of tissue in accordance with a set of modulation parameters and provide the desired efficacious therapy to the patient. The best modulation parameter set will typically be one that delivers stimulation energy to the volume of tissue that must be stimulated in order to provide the therapeutic benefit (e.g., treatment of pain), while minimizing the volume of non-target tissue that is stimulated.

The clinician generally programs the neuromodulation device through a computerized programming system. This programming system can be a self-contained hardware/software system, or can be defined predominantly by software running on a standard personal computer (PC). The PC or custom hardware may actively control the characteristics of the electrical stimulation generated by the neuromodulation device to allow the optimum modulation parameters to be determined based on patient feedback or other means and to subsequently program the neuromodulation device with the optimum modulation parameter set or sets. The computerized programming system may be operated by a clinician attending the patient in several scenarios.

One known computerized programming system for SCS is called the Bionic Navigator®, available from Boston Scientific Neuromodulation Corporation. The Bionic Navigator® is a software package that operates on a suitable PC and allows clinicians to program modulation parameters into an external handheld programmer (referred to as a remote control). Each set of modulation parameters, including fractionalized current distribution to the electrodes (as percentage cathodic current, percentage anodic current, or off), may be stored in both the Bionic Navigator® and the remote control and combined into a stimulation program that can then be used to stimulate multiple regions within the patient.

A typical transverse section of the spinal cord will include a central "butterfly" shaped central area of gray matter (neuronal cell bodies) substantially surrounded by an ellipse-shaped outer area of white matter (myelinated axons). The dorsal horns are the dorsal portions of the "butterfly" shaped central area of gray matter, which includes neuronal cell terminals, neuronal cell bodies, dendrites, and axons. Conventional SCS programming has as its therapeutic goal maximal stimulation (i.e., recruitment) of dorsal column fibers that run in the white matter along the longitudinal axis of the spinal cord and minimal stimulation of other fibers that run perpendicular to the longitudinal axis of the spinal cord (dorsal root fibers, predominantly). The white matter of the dorsal column includes mostly large myelinated axons that form afferent fibers.

While fibers in the dorsal column run in an axial direction, fibers in the dorsal horn can be oriented in many directions, including perpendicular to the longitudinal axis of the spinal cord. Dorsal horn fibers are also a different distance from the typically placed epidural SCS leads, when compared to dorsal column fibers.

Further, dorsal horn fibers and dorsal column fibers have different responses to electrical stimulation. The strength of stimulation (i.e., depolarizing or hyperpolarizing) of the dorsal column fibers and neurons is described by the so-called "activating function" $\partial V/\partial x^2$ which is proportional to the second-order spatial derivative of the voltage along the longitudinal axis of the spine. This is partially because the large myelinated axons in dorsal column are primarily aligned longitudinally along the spine. On the other hand, the likelihood of generating action potentials in dorsal horn fibers and neurons is described by the "activating function" $\partial V/\partial x$ (otherwise known as the electric field). The dorsal horn "activating function" is proportional not to the second-order derivative, but to the first-order derivative of the voltage along the fiber axis. Accordingly, distance from the electrical field locus affects the dorsal horn "activating function" less than it affects the dorsal column "activating function."

Current implantable neuromodulation systems typically include electrodes implanted adjacent to the dorsal column of the spinal cord of the patient. Current implantable neuromodulation systems are also typically programmed to deliver stimulation energy to the spinal without differentiating between the dorsal column and the dorsal horn of the spinal cord of the patient. While generally stimulation of neuronal elements (e.g., neurons, dendrites, axons, cell bodies, and neuronal cell terminals) in the patient's spinal cord provides therapy for pain, such stimulation sometimes causes alternative or artifactual sensations (e.g., paresthesia), which are sometime unwelcomed by the patient. Such stimulation also requires (1) selective lead placement, as described above, (2) optimal stimulating electrode selection, and (3) optimization of electrode configuration (e.g., polarity and anode-cathode separation). Accordingly, these exists a need for implantable neuromodulation systems and modulation parameter sets for same that provide therapy for pain while minimizing alternative or artifactual sensations and the sensitivity of the system to modulation parameters. There also exists a need for an implantable neuromodulation systems and modulation parameter sets for same that preferentially stimulate dorsal horn neuronal elements over dorsal column neuronal elements.

Current implantable neuromodulation methods also include an electrical field localization step, in which the longitudinal location of the electrical field locus is identified through trial and error and with patient feedback. While electrical field localization provides effective neuromodulation, the process is time-consuming and requires patient participation. Further, when an electrical modulation lead shifts, repeating electrical field localization may be required. Accordingly, there exists a need for implantable neuromodulation systems and parameter sets for effective neuromodulation while minimizing the need for electrical field localization.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

SUMMARY OF THE INVENTION

Figure 1:
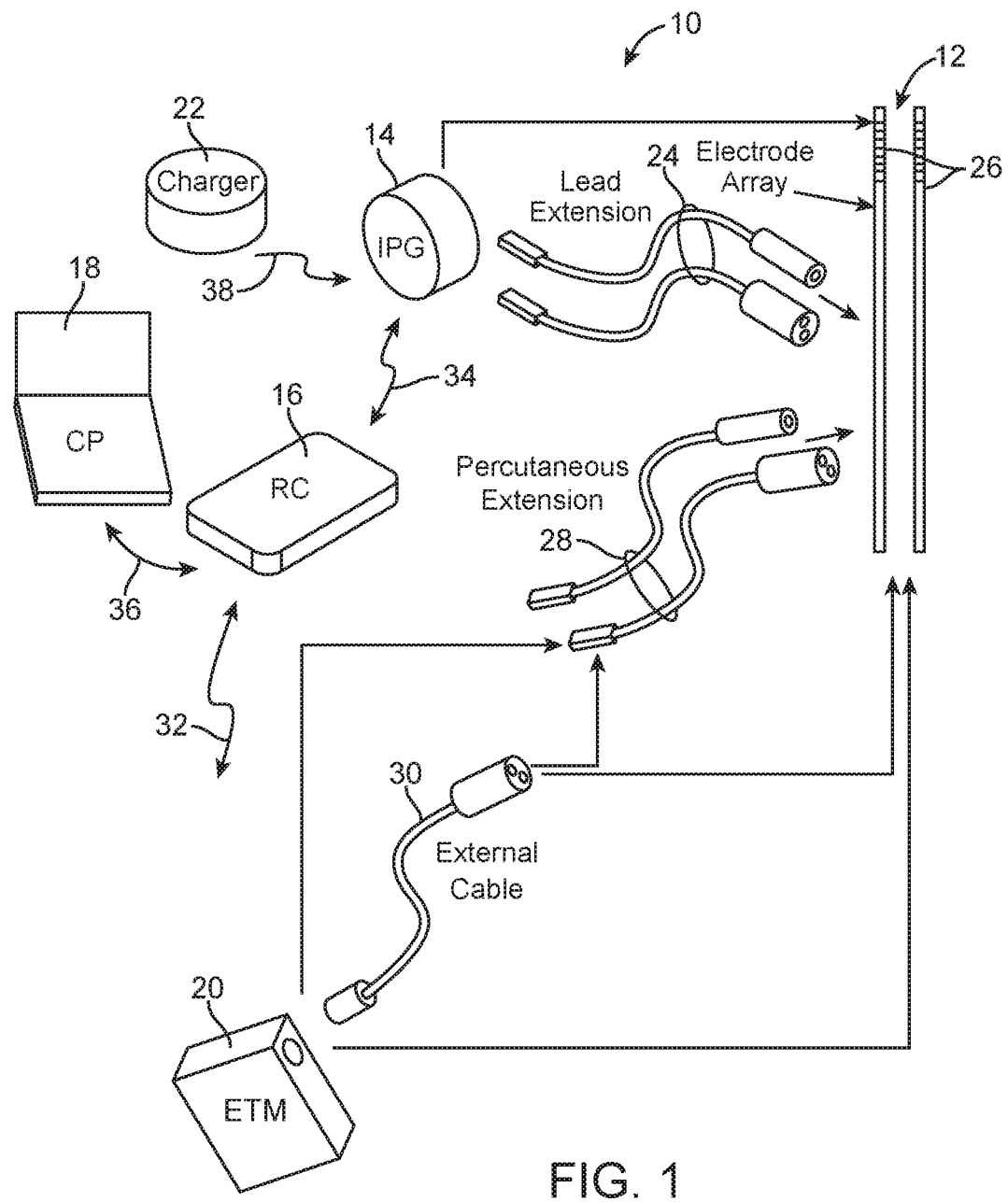
FIG. 1 is a plan view of a Spinal Cord Modulation (SCM) system constructed in accordance with one embodiment of the present inventions.

In accordance with a first aspect of the present inventions, a method of operating an implantable neuromodulator coupled to an electrode array implanted adjacent tissue of a patient having a medical condition is provided. The method comprises conveying electrical modulation energy to tissue of the patient in accordance with a modulation parameter set, wherein conveying the electrical modulation energy to tissue of the patient in accordance with the modulation parameter set stimulates dorsal horn neuronal elements more than dorsal column neuronal elements.

In one embodiment, conveying the electrical modulation energy to tissue of the patient in accordance with the modulation parameter set generates an electrical field having a locus disposed adjacent a dorsal horn of a spinal cord of the patient. The locus may be disposed closer to the dorsal horn of the spinal cord of the patient than an ipsilateral dorsal column of the spinal cord of the patient, wherein the dorsal column is adjacent the dorsal horn. The electrical modulation energy may be conveyed through electrodes on an implanted electrical modulation lead, and conveying the electrical modulation energy to tissue of the patient in accordance with the modulation parameter set may stimulate dorsal horn neuronal elements along a substantial portion (i.e., more than 80%) of the implanted electrical modulation lead.

In another embodiment, conveying the electrical modulation energy to tissue of the patient in accordance with the modulation parameter set generates an electrical field, wherein a first component of the electrical field extends along a spinal cord of the patient, wherein a second component of the electrical field extends transverse to the spinal cord of the patient, and wherein a first gradient across the first component of the electrical field renders the dorsal column neuronal elements less excitable than a second gradient across the second component of the electrical field renders the dorsal horn neuronal elements.

In another embodiment, conveying the electrical modulation energy to tissue of the patient in accordance with the modulation parameter set generates an electrical field, wherein a first component of the electrical field extends along a spinal cord of the patient, wherein a second component of the electrical field extends transverse to the spinal cord of the patient, and wherein a second gradient across the first component of the electrical field is weaker than a first gradient across the second component of the electrical field.

In still another embodiment, conveying the electrical modulation energy to tissue of the patient in accordance with the modulation parameter set generates a first driving force in dorsal horn neuronal elements that is stronger than a second driving force in dorsal column neuronal elements.

In yet another embodiment, the modulation parameter set defines an electrode combination. The electrode combination may comprise a fractionalized electrode combination. The fractionalized electrode combination may be configured such that all electrodes on an electrical modulation lead have the same polarity. The fractionalized electrode combination may be configured such that a plurality of electrodes on an electrical modulation lead all have the same polarity, and no electrode on the electrical modulation lead has the opposite polarity. The plurality of electrodes may be disposed adjacent to each other on the electrical modulation lead. The plurality of electrodes may have three, four, or five electrodes. The fractionalized electrode combination may be configured such that all electrodes on the electrical modulation lead are anodes or cathodes. The fractionalized electrode combination may be configured such that an equal amount or unequal amounts of current is directed to each electrode on the electrical modulation lead.

The fractionalized electrode combination may be further configured such that the same neuronal driving force is directed to each electrode of the plurality. The method may further comprise calculating a driving force directed to each electrode of the plurality by calibrating each electrode of the plurality.

In still another embodiment, conveying the electrical modulation energy to tissue of the patient in accordance with the modulation parameter set generates an electrical field having an elongated shape disposed over a dorsal horn of a spinal cord of the patient, and the elongated shape has a longitudinal axis parallel to the spinal cord of the patient. The elongated shape may taper at the one or both ends thereof.

In accordance with a second aspect of the present inventions, a method of operating an implantable neuromodulator coupled to an electrode array implanted adjacent tissue of a patient having a medical condition is provided. The method comprises conveying electrical modulation energy to tissue of the patient in accordance with a modulation parameter set, wherein conveying the electrical modulation energy to tissue of the patient in accordance with the modulation parameter set stimulates dorsal horn neuronal elements more than dorsal column neuronal elements. The method also comprises determining a perception threshold for electrical modulation energy conveyed through each electrode of a plurality of electrodes on an electrical modulation lead; modifying a neuronal driving force indicator for electrical modulation energy conveyed through each electrode of the plurality based on the respective determined perception threshold. The method further comprises modifying the modulation parameter set based on the modified neuronal driving force indicator for electrical modulation energy conveyed through each electrode of the plurality before conveying electrical modulation energy to tissue of the patient in accordance with the modulation parameter set.

In one embodiment, the neuronal driving force indicator is an activating function. The activating function may be a continuous activating function determined by calculating the second-order spatial derivative of the extracellular potential along an axon. The activating function may be a discrete activating function estimating by the formula: $AF(n)=G_a/(\pi \times d \times l) \times [V_e(n-1)-2\ V_e(n)+V_e(n+1)]$, wherein $G_a$ is the axonal internodal conductance, d is the axonal diameter, l is the length of the node of Ranvier, $V_e(n)$ is the strength of the electric field at the node for which the activating function is determined, $V_e(n-1)$ is the strength of the electric field at the node preceding the node for which the activating function is determined, and $V_e(n+1)$ is the strength of the electric field at the node following the node for which the activating function is determined. The proportionality constants in the above formula may be eliminated from the equation and result in identical optimization.

In another embodiment, the neuronal driving force indicator may be a total driving function ("TDF"), which is a linear combination of the activating function at multiple nodes. The TDF is described in U.S. Patent Application Ser. Nos. 61/427,027 and 61/427,059, both filed on Dec. 23, 2010. Further details discussing the modeling of neuronal elements in response to an induced electric field are described in U.S. Pat. No. 7,627,384, Eduardo N. Warman, Modeling the Effects of Electric Fields on Nerve Fibers: Determination of Excitation Thresholds, IEEE Transactions on Biomedical Engineering, Vol. 39, No. 12, December 1992, and U.S. Patent Application Ser. No. 61/427,059, filed Dec. 23, 2010. All of the references identified in this paragraph are expressly incorporated herein by reference as though set forth in full.

In another embodiment, the method also comprises estimating the current fractionalization by minimizing the integral of the square of the discrete activating function over a longitudinal axis of the electrical modulation lead while maximizing the electric field over the dorsal horn of the spinal cord of the patient, to thereby minimize the discrete activating function of the dorsal column neuronal elements. The method may further comprises estimating the current fractionalization by minimizing the sum of the square of the discrete activating function divided by the determined perception threshold at each electrode on an electrical modulation lead. The perception threshold may be determined using patient feedback. The perception threshold may also be determined by measuring local field potentials (action potentials) at an electrode of the plurality, or evoked potentials at distance (e.g., at the cortex in the brain). The electrode may be the same electrode through which electrical modulation energy is conveyed to determine the perception threshold. Conveying the electrical modulation energy to tissue of the patient in accordance with the modified modulation parameter set may generates a modified electrical field, wherein conveying the electrical modulation energy to tissue of the patient in accordance with the modulation parameter set before modification generates a non-modified electrical field, and wherein a first gradient across a component of the modified electrical field extending along a spinal cord of the patient is weaker than a second gradient across a component of the non-modified electrical field extending along the spinal cord of the patient. In other words, the modified electrical field (by taking the perception threshold into account) generates a longitudinal field gradient that is less than the longitudinal field gradient generated by a non-modified electrical field.

In accordance with a third aspect of the present inventions, a method of operating an implantable neuromodulator coupled to an electrode array implanted adjacent tissue of a patient having a medical condition is provided. The method comprises implanting a first electrical modulation lead adjacent a dorsal horn of a spinal cord of the patient. The method also comprises implanting a second electrical modulation lead adjacent a dorsal column of the spinal cord of the patient. The method further comprises conveying electrical modulation energy through the first and second electrical modulation leads to tissue of the patient in accordance with a modulation parameter set, wherein the electrical modulation energy conveyed in accordance with the modulation parameter set stimulates dorsal horn neuronal elements more than dorsal column neuronal elements.

In some embodiments, conveying the electrical modulation energy to tissue of the patient in accordance with the modulation parameter set does not cause the patient to perceive paresthesia in response to the conveyed electrical modulation energy.

Other and further aspects and features of the invention will be evident from reading the following detailed description of the preferred embodiments, which are intended to illustrate, not limit, the invention.

DETAILED DESCRIPTION OF THE EMBODIMENTS

Turning first to FIG. 1, an exemplary SCM system 10 generally includes a plurality (in this case, two) of implantable neuromodulation leads 12, an implantable pulse generator (IPG) 14, an external remote controller RC 16, a clinician's programmer (CP) 18, an external trial modulator (ETM) 20, and an external charger 22.

The IPG 14 is physically connected via one or more percutaneous lead extensions 24 to the neuromodulation leads 12, which carry a plurality of electrodes 26 arranged in an array. In the illustrated embodiment, the neuromodulation leads 12 are percutaneous leads, and to this end, the electrodes 26 are arranged in-line along the neuromodulation leads 12. The number of neuromodulation leads 12 illustrated is two, although any suitable number of neuromodulation leads 12 can be provided, including only one, as long as the number of electrodes 26 is greater than two (including the IPG case) to allow for lateral steering of the current. Alternatively, a surgical paddle lead can be used in place of one or more of the percutaneous leads. As will be described in further detail below, the IPG 14 includes pulse generation circuitry that delivers electrical modulation energy in the form of a pulsed electrical waveform (i.e., a temporal series of electrical pulses) to the electrode array 26 in accordance with a set of modulation parameters.

The ETM 20 may also be physically connected via the percutaneous lead extensions 28 and external cable 30 to the neuromodulation leads 12. The ETM 20, which has similar pulse generation circuitry as the IPG 14, also delivers electrical modulation energy in the form of a pulse electrical waveform to the electrode array 26 accordance with a set of modulation parameters. The major difference between the ETM 20 and the IPG 14 is that the ETM 20 is a non-implantable device that is used on a trial basis after the neuromodulation leads 12 have been implanted and prior to implantation of the IPG 14, to test the responsiveness of the modulation that is to be provided. Thus, any functions described herein with respect to the IPG 14 can likewise be performed with respect to the ETM 20. For purposes of brevity, the details of the ETM 20 will not be described herein. Details of exemplary embodiments of ETM are disclosed in U.S. Pat. No. 6,895,280, which is expressly incorporated herein by reference.

The RC 16 may be used to telemetrically control the ETM 20 via a bi-directional RF communications link 32. Once the IPG 14 and neuromodulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. As will be described in further detail below, the CP 18 provides clinician detailed modulation parameters for programming the IPG 14 and ETM 20 in the operating room and in follow-up sessions.

The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown). The clinician detailed modulation parameters provided by the CP 18 are also used to program the RC 16, so that the modulation parameters can be subsequently modified by operation of the RC 16 in a stand-alone mode (i.e., without the assistance of the CP 18).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present. For purposes of brevity, the details of the external charger 22 will not be described herein. Details of exemplary embodiments of the external charger are disclosed in U.S. Pat. No. 6,895,280, which is expressly incorporated herein by reference.

Figure 2:
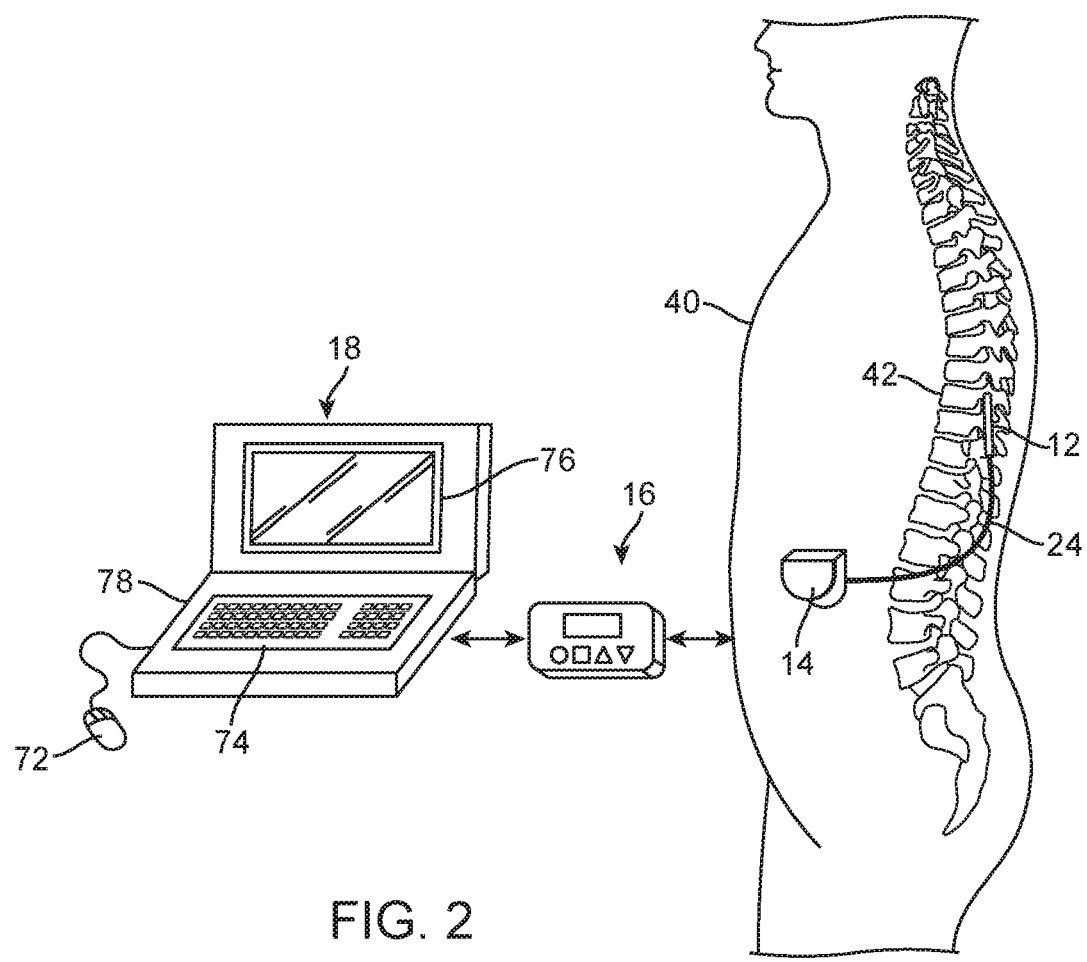
FIG. 2 is a plan view of the SCM system of FIG. 1 in use with a patient.

As shown in FIG. 2, the neuromodulation leads 12 are implanted within the spinal column 42 of a patient 40. The preferred placement of the neuromodulation leads 12 is adjacent, i.e., resting upon, the spinal cord area to be stimulated. Due to the lack of space near the location where the neuromodulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neuromodulation leads 12. As shown in FIG. 2, the CP 18 communicates with the IPG 14 via the RC 16.

Figure 3:
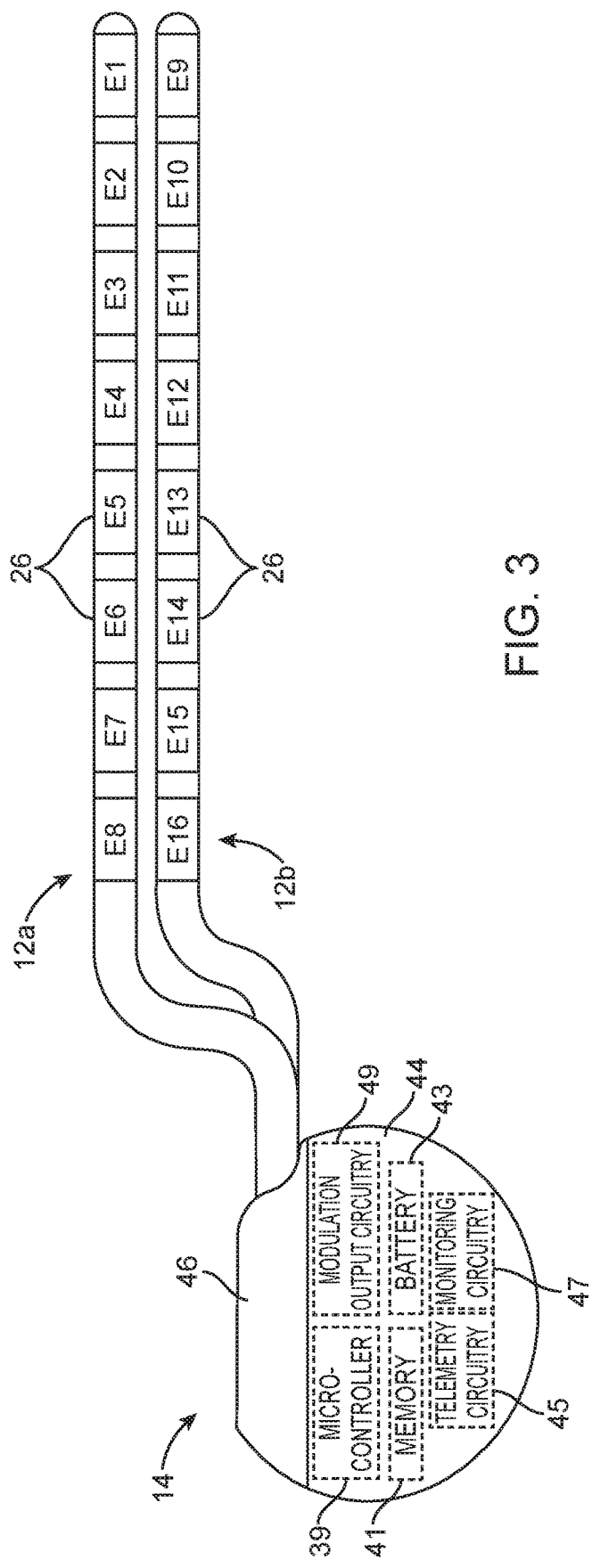
FIG. 3 is a profile view of an implantable pulse generator (IPG) and percutaneous leads used in the SCM system of FIG. 1.

Referring now to FIG. 3, the external features of the neuromodulation leads 12 and the IPG 14 will be briefly described. One of the neuromodulation leads 12a has eight electrodes 26 (labeled E1-E8), and the other neuromodulation lead 12b has eight electrodes 26 (labeled E9-E16). The actual number and shape of leads and electrodes will, of course, vary according to the intended application. The IPG 14 comprises an outer case 44 for housing the electronic and other components (described in further detail below), and a connector 46 to which the proximal ends of the neuromodulation leads 12 mates in a manner that electrically couples the electrodes 26 to the electronics within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

The IPG 14 comprises electronic components, such as a controller/processor (e.g., a microcontroller) 39, memory 41, a battery 43, telemetry circuitry 45, monitoring circuitry 47, modulation output circuitry 49, and other suitable components known to those skilled in the art. The microcontroller 39 executes a suitable program stored in memory 41, for directing and controlling the neuromodulation performed by IPG 14. Telemetry circuitry 45, including an antenna (not shown), is configured for receiving programming data (e.g., the operating program and/or modulation parameters) from the RC 16 and/or CP 18 in an appropriate modulated carrier signal, which the programming data is then stored in the memory (not shown). The telemetry circuitry 45 is also configured for transmitting status data to the RC 16 and/or CP 18 in an appropriate modulated carrier signal. The battery 43, which may be a rechargeable lithium-ion or lithium-ion polymer battery, provides operating power to IPG 14. The monitoring circuitry 47 is configured for monitoring the present capacity level of the battery 43.

The modulation output circuitry 49 provides electrical modulation energy in the form of a pulsed electrical waveform to the electrodes 26 in accordance with a set of modulation parameters programmed into the IPG 14. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse width (measured in microseconds), pulse rate (measured in pulses per second), and burst rate (measured as the modulation on duration X and modulation off duration Y).

Electrical modulation will occur between a plurality of activated electrodes, one of which may be the IPG case 44. The system 10 is capable of transmitting modulation energy to the tissue in a monopolar or multipolar (e.g., bipolar, tripolar, etc.) fashion, but monopolar modulation is used in the disclosed method. Monopolar modulation occurs when a selected one of the lead electrodes 26 is activated along with the case of the IPG 14, so that modulation energy is transmitted between the selected electrode 26 and case.

Any of the electrodes E1-E16 and case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels.

In the illustrated embodiment, IPG 14 can individually control the magnitude of electrical current flowing through each of the electrodes. In this case, it is preferred to have a current generator, wherein individual current-regulated amplitudes from independent current sources for each electrode may be selectively generated. Although this system is optimal to take advantage of the invention, other neuromodulators that may be used with the invention include neuromodulators having voltage regulated outputs. While individually programmable electrode amplitudes are optimal to achieve fine control, a single output source switched across electrodes may also be used, although with less fine control in programming. Mixed current and voltage regulated devices may also be used with the invention. Further details discussing the detailed structure and function of IPGs are described more fully in U.S. Pat. Nos. 6,516,227 and 6,993,384, which are expressly incorporated herein by reference.

It should be noted that rather than an IPG, the SCM system 10 may alternatively utilize an implantable receiver-stimulator (not shown) connected to the neuromodulation leads 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-modulator. The implanted receiver-modulator receives the signal and generates the modulation in accordance with the control signals.

The IPG 14 may be operated in one of a super-threshold delivery mode and a sub-threshold delivery mode. While in the super-threshold delivery mode, the IPG 14 is configured for delivering electrical modulation energy that provides super-threshold therapy to the patient (in this case, causes the patient to perceive paresthesia). While in the sub-threshold delivery mode, the IPG 14 is configured for delivering electrical modulation energy that provides sub-threshold therapy to the patient (in this case, does not cause the patient to perceive paresthesia). Further details discussing modulation phases and delivery modes are described more fully in U.S. Provisional Patent Application Ser. No. 61/801,917, entitled "Systems and Methods for Delivering Sub-Threshold Therapy to a Patient," which is expressly incorporated herein by reference.

As briefly discussed above, the CP 18 greatly simplifies the programming of multiple electrode configurations, allowing the user (e.g., the physician or clinician) to readily determine the desired modulation parameters to be programmed into the IPG 14, as well as the RC 16. Thus, modification of the modulation parameters in the programmable memory of the IPG 14 after implantation is performed by a user using the CP 18, which can directly communicate with the IPG 14 or indirectly communicate with the IPG 14 via the RC 16. That is, the CP 18 can be used by the user to modify operating parameters of the electrode array 26 near the spinal cord.

As shown in FIG. 2, the overall appearance of the CP 18 is that of a laptop personal computer (PC), and in fact, may be implemented using a PC that has been appropriately configured to include a directional-programming device and programmed to perform the functions described herein. Alternatively, the CP 18 may take the form of a mini-computer, personal digital assistant (PDA), etc., or even a remote control (RC) with expanded functionality. Thus, the programming methodologies can be performed by executing software instructions contained within the CP 18. Alternatively, such programming methodologies can be performed using firmware or hardware. In any event, the CP 18 may actively control the characteristics of the electrical stimulation generated by the IPG 14 to allow the optimum modulation parameters to be determined based on patient feedback and for subsequently programming the IPG 14 with the optimum modulation parameter.

To allow the user to perform these functions, the CP 18 includes a user input device (e.g., a mouse 72 and a keyboard 74), and a programming display screen 76 housed in a case 78. It is to be understood that in addition to, or in lieu of, the mouse 72, other directional programming devices may be used, such as a trackball, touchpad, joystick, or directional keys included as part of the keys associated with the keyboard 74.

In the illustrated embodiment described below, the display screen 76 takes the form of a conventional screen, in which case, a virtual pointing device, such as a cursor controlled by a mouse, joy stick, trackball, etc., can be used to manipulate graphical objects on the display screen 76. In alternative embodiments, the display screen 76 takes the form of a digitizer touch screen, which may either passive or active. If passive, the display screen 76 includes detection circuitry (not shown) that recognizes pressure or a change in an electrical current when a passive device, such as a finger or non-electronic stylus, contacts the screen. If active, the display screen 76 includes detection circuitry that recognizes a signal transmitted by an electronic pen or stylus. In either case, detection circuitry is capable of detecting when a physical pointing device (e.g., a finger, a non-electronic stylus, or an electronic stylus) is in close proximity to the screen, whether it be making physical contact between the pointing device and the screen or bringing the pointing device in proximity to the screen within a predetermined distance, as well as detecting the location of the screen in which the physical pointing device is in close proximity. When the pointing device touches or otherwise is in close proximity to the screen, the graphical object on the screen adjacent to the touch point is "locked" for manipulation, and when the pointing device is moved away from the screen the previously locked object is unlocked. Further details discussing the use of a digitizer screen for programming are set forth in U.S. Provisional Patent Application Ser. No. 61/561, 760, entitled "Technique for Linking Electrodes Together during Programming of Neurostimulation System," which is expressly incorporated herein by reference.

Figure 4:
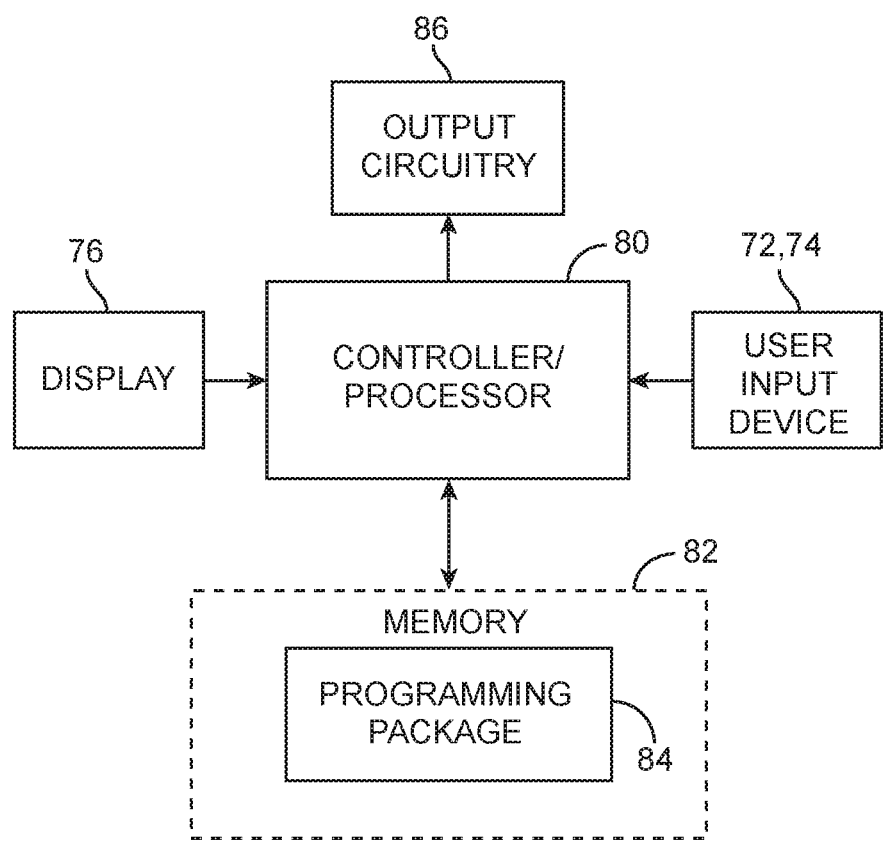
FIG. 4 is a block diagram of the internal components of a clinician's programmer (CP) used in the SCM system of FIG. 1.

As shown in FIG. 4, the CP 18 includes a controller/processor 80 (e.g., a central processor unit (CPU)) and memory 82 that stores a stimulation programming package 84, which can be executed by the controller/processor 80 to allow the user to program the IPG 14, and RC 16. The CP 18 further includes an output circuitry 86 for downloading modulation parameters to the IPG 14 and RC 16 and for uploading modulation parameters already stored in the memory 66 of the RC 16 or memory of the IPG 14. In addition, the CP 18 further includes a user input device 88 (such as the mouse 72 or keyboard 74) to provide user commands. Notably, while the controller/processor 80 is shown in FIG. 4 as a single device, the processing functions and controlling functions can be performed by a separate controller and processor 64. Thus, it can be appreciated that the controlling functions described below as being performed by the CP 18 can be performed by a controller, and the processing functions described below as being performed by the CP 18 can be performed by the processor 64.

Execution of the programming package 84 by the controller/processor 80 provides a multitude of display screens (not shown) that can be navigated through via use of the mouse 72. These display screens allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical modulation energy output by the neuromodulation leads 12, and select and program the IPG 14 with modulation parameters in both a surgical setting and a clinical setting. Further details discussing the above-described CP functions are disclosed in U.S. patent application Ser. No. 12/501,282, entitled "System and Method for Converting Tissue Stimulation Programs in a Format Usable by an Electrical Current Steering Navigator," and U.S. patent application Ser. No. 12/614,942, entitled "System and Method for Determining Appropriate Steering Tables for Distributing Modulation energy Among Multiple Neuromodulation Electrodes," which are expressly incorporated herein by reference. Execution of the programming package 84 provides a user interface that conveniently allows a user to program the IPG 14.

Figure 5:
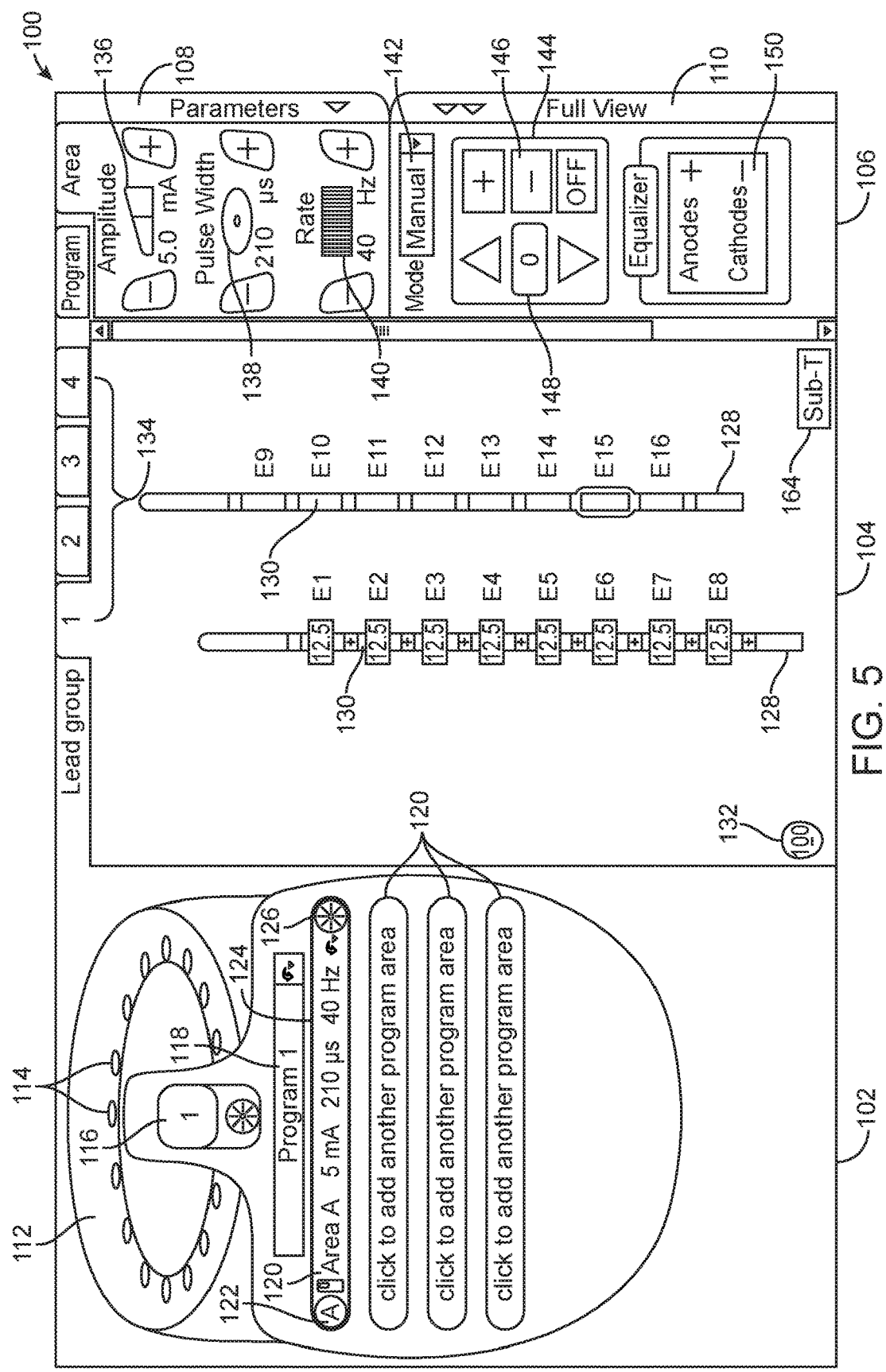
FIG. 5 is a plan view of a user interface of the CP of FIG. 4 for programming the IPG of FIG. 3 in a manual programming mode.

Referring to FIG. 5, a graphical user interface (GUI) 100 that can be generated by the CP 18 to allow a user to program the IPG 14 will be described. In the illustrated embodiment, the GUI 100 comprises three panels: a program selection panel 102, a lead display panel 104, and a modulation parameter adjustment panel 106. Some embodiments of the GUI 100 may allow for closing and expanding one or both of the lead display panel 102 and the parameter adjustment panel 106 by clicking on the tab 108 (to show or hide the parameter adjustment panel 106) or the tab 110 (to show or hide the full view of both the lead selection panel 104 and the parameter adjustment panel 106).

The program selection panel 102 provides information about modulation programs and coverage areas that have been, or may be, defined for the IPG 14. In particular, the program selection panel 102 includes a carousel 112 on which a plurality of modulation programs 114 (in this case, up to sixteen) may be displayed and selected. The program selection panel 102 further includes a selected program status field 116 indicating the number of the modulation program 114 that is currently selected (any number from "1" to "16"). In the illustrated embodiment, program 1 is the only one currently selected, as indicated by the number "1" in the field 116. The program selection panel 102 further comprises a name field 118 in which a user may associate a unique name to the currently selected modulation program 114. In the illustrated embodiment, currently selected program 1 has been called "lower back," thereby identifying program 1 as being the modulation program 114 designed to provide therapy for lower back pain.

The program selection panel 102 further comprises a plurality of coverage areas 120 (in this case, up to four) with which a plurality of modulation parameter sets can respectively be associated to create the currently selected modulation program 114 (in this case, program 1). Each coverage area 120 that has been defined includes a designation field 122 (one of letters "A"-"D"), and an electrical pulse parameter field 124 displaying the electrical pulse parameters, and specifically, the pulse amplitude, pulse width, and pulse rate, of the modulation parameter set associated with the that coverage area. In this example, only coverage area A is defined for program 1, as indicated by the "A" in the designation field 122. The electrical pulse parameter field 124 indicates that a pulse amplitude of 5 mA, a pulse width of 210 μs, and a pulse rate of 40 Hz has been associated with coverage area A.

Each of the defined coverage areas 120 also includes a selection icon 126 that can be alternately actuated to activate or deactivate the respective coverage area 120. When a coverage area is activated, an electrical pulse train is delivered from the IPG 14 to the electrode array 26 in accordance with the modulation parameter set associated with that coverage area. Notably, multiple ones of the coverage areas 120 can be simultaneously activated by actuating the selection icons 126 for the respective coverage areas. In this case, multiple electrical pulse trains are concurrently delivered from the IPG 14 to the electrode array 26 during timing channels in an interleaved fashion in accordance with the respective modulation parameter sets associated with the coverage areas 120. Thus, each coverage area 120 corresponds to a timing channel.

To the extent that any of the coverage areas 120 have not been defined (in this case, three have not been defined), they include text "click to add another program area"), indicating that any of these remaining coverage areas 120 can be selected for association with a modulation parameter set. Once selected, the coverage area 120 will be populated with the designation field 122, electrical pulse parameter field 124, and selection icon 126.

Figure 10:
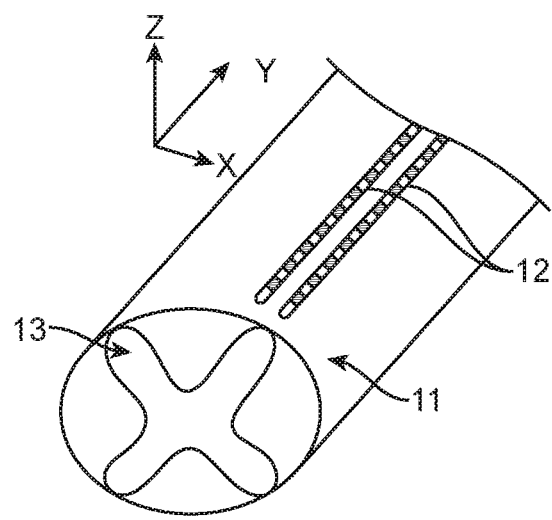
FIG. 10 is a schematic view of two electrical modulation leads implanted adjacent a spinal cord in accordance with one embodiment of the present inventions.

The lead display panel 104 includes graphical leads 128, which are illustrated with eight graphical electrodes 130 each (labeled electrodes E1-E8 for the first lead 128 and electrodes E9-E16 for second lead 128, see FIG. 10 for corresponding modulation leads 12). The lead display panel 104 also includes a graphical case 132 representing the case 44 of the IPG 14. The lead display panel 104 further includes lead group selection tabs 134 (in this case, four), any of which can be actuated to select one of four groups of graphical leads 128. In this case, the first lead group selection tab 134 has been actuated, thereby displaying the two graphical leads 128 in their defined orientation. In the case where additional leads 12 are implanted within the patient, they can be associated with additional lead groups.

The parameters adjustment panel 106 also includes a pulse amplitude adjustment control 136 (expressed in milliamperes (mA)), a pulse width adjustment control 138 (expressed in microseconds (μs)), and a pulse rate adjustment control 140 (expressed in Hertz (Hz)), which are displayed and actuatable in all the programming modes. Each of the controls 136-140 includes a first arrow that can be actuated to decrease the value of the respective modulation parameter and a second arrow that can be actuated to increase the value of the respective modulation parameter. Each of the controls 136-140 also includes a display area for displaying the currently selected parameter. In response to the adjustment of any of electrical pulse parameters via manipulation of the graphical controls in the parameter adjustment panel 106, the controller/processor 80 generates a corresponding modulation parameter set (with a new pulse amplitude, new pulse width, or new pulse rate) and transmits it to the IPG 14 via the telemetry circuitry 86 for use in delivering the modulation energy to the electrodes 26.

The parameter adjustment panel 106 includes a pull-down programming mode field 142 that allows the user to switch between several programming modes, including a manual programming mode. Each of these programming modes allows a user to define a modulation parameter set for the currently selected coverage area 120 of the currently selected program 114 via manipulation of graphical controls in the parameter adjustment panel 106 described above, as well as the various graphical controls described below. In the illustrated embodiment, when switching between programming modes via actuation of the programming mode field 142, the last electrode configuration with which the IPG 14 was programmed in the previous programming mode is converted into another electrode configuration, which is used as the first electrode configuration with which the IPG 14 is programmed in the subsequent programming mode.

Using the CP 18, a user (e.g., a physician) instructs the IPG 14 to generate a modulation signal resulting in an electrical field having a locus. The user can use either the manual programming mode (described in examples below) of the CP 18 to set various modulation parameters. The electrical field locus can be displaced by fractionalizing the cathodic current across the array of electrodes 26. Other modulation parameters (e.g., amplitude, frequency, duty cycle, pulse width, etc.) can also be adjusted.

Having described the hardware and software of the SCM system 10, placement of the electrical modulation lead 12 and the corresponding electrical fields will now be described. FIGS. 6-9 illustrate the difference in electrical field strength in the longitudinal and transverse directions when the current is fractionalized such that the electrical field in the longitudinal direction generated by the fractionalized current delivered to each electrode 26 is approximately equal. The voltage at a patient's spinal cord 11 (especially at the dorsal column fibers) is approximately equal in the longitudinal direction, resulting in a voltage gradient of approximately zero along the dorsal column. However that may correspond to different amounts of fractionalized current delivered to each electrode 26. Calibration techniques (also described below) are used to determine the proper current fractionalization. With the current fractionalized to a plurality of electrodes 26 on the electrical modulation lead 12, the resulting field can be calculated by superimposing the fields generated by the current delivered to each electrode 26. Moreover each electrical field has a longitudinal component and a transverse component.

Figure 6:
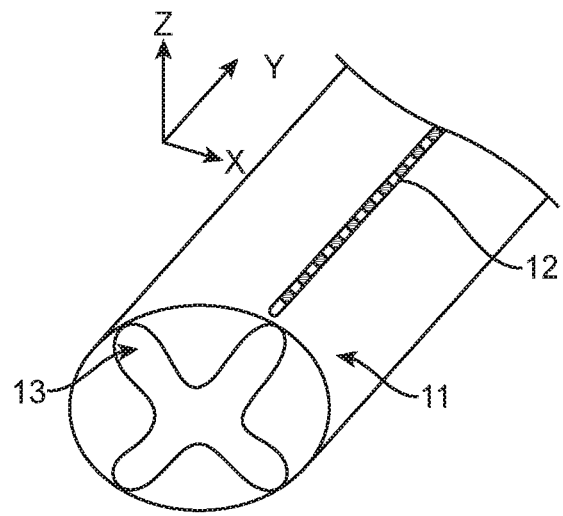
FIG. 6 is a schematic view of an electrical modulation lead implanted adjacent a spinal cord in accordance with one embodiment of the present inventions.

FIG. 6 is a schematic view of a single electrical modulation lead 12 implanted over approximately the longitudinal midline of the patient's spinal cord 11. Longitudinal component of the electrical field is directed along the y-axis depicted in FIG. 6, and a transverse component of the electrical field is directed along the x-axis depicted in FIG. 6.

Figure 7:
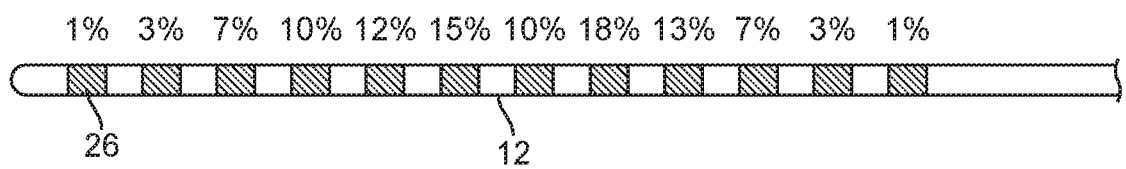
FIG. 7 is a schematic view of an electrical modulation lead in accordance with one embodiment of the present inventions.

FIG. 7 is a schematic view of the electrical modulation lead 12 showing the fractionalization of the anodic current delivered to the electrodes 26 on the electrical modulation lead 12. As in FIG. 5, the outer case 44 of the IPG 14 is the only cathode, and carries 100% of the cathodic current. The fractionalization of the anodic current shown in FIG. 7 does not deliver an equal amount of current to each electrode 26, because this embodiment takes into account the differences in how the tissue underlying each electrode 26 reacts to electrical stimulation (described below). Also, the ends of the portion of the electrical modulation lead 12 at include electrodes 26 having lower gradient in the longitudinal direction. The magnitude of the electrical field tapers down at the ends of the electrical modulation lead 12. Fractionalization of the current to the electrodes 26 is controlled such that the tissue underlying each electrode 26 in the middle portion of the electrical modulation lead 12 reacts approximately equally to the electrical stimulation, or tissue activation underlying each electrode are eliminated. However, the resulting fractionalization is not equal. In the embodiment shown in FIG. 7, fractionalization of the current to the middle electrodes 26 varies from 10% to 18%, reflecting the variation in the tissue underlying those electrodes 26. The fractionalization across the electrical modulation lead 12 can vary in any manner as long as the total of fractionalized currents equals 100%.

Figure 8:
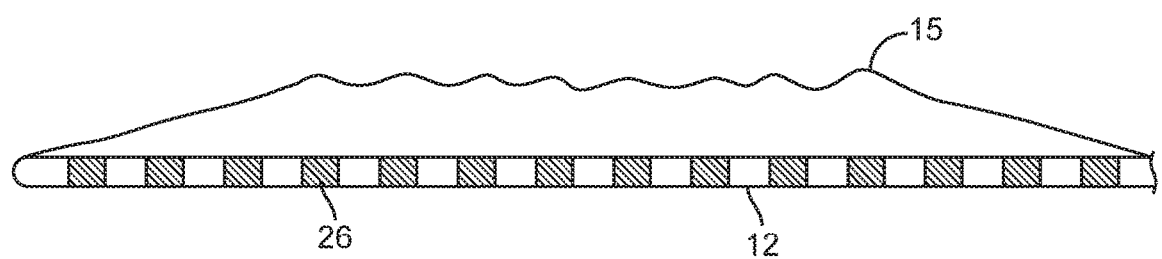
FIG. 8 is a plot of a longitudinal component of an electrical field superimposed over a schematic view of an electrical modulation lead in accordance with one embodiment of the present inventions.

The gradient in the longitudinal direction along the axis of the electrical modulation lead 12 is schematically illustrated in FIG. 8. In FIG. 8, the electrical field strength 15 in the longitudinal direction is plotted over a schematic representation of the electrical modulation lead 12. FIG. 8 shows that the electrical field strength 15 is substantially constant over the middle portion of the electrical modulation lead 12, but may form a wave with very small amplitude because of the gaps between the electrodes 26 in the lead 12. This substantially constant electrical field forms a small longitudinal gradient, which minimizes activation of the large myelinated axons in the dorsal column. FIG. 8 also shows the electrical field in the longitudinal direction tapering at the ends of the electrical modulation lead 12.

Figure 9:
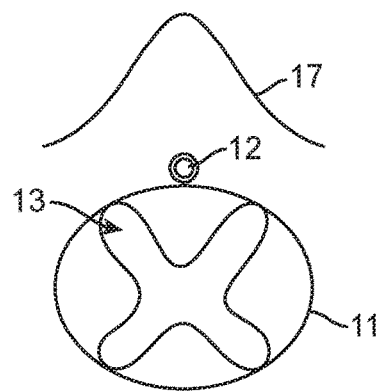
FIG. 9 is a plot of a transverse component of an electrical field superimposed over a schematic view of an electrical modulation lead implanted adjacent a spinal cord in accordance with one embodiment of the present inventions.

The gradient in the transverse direction is schematically illustrated in FIG. 9. In FIG. 9, the transverse electrical field strength 17 in the transverse direction is plotted over a schematic representation of the electrical modulation lead 12 and the spinal cord 11 of the patient. FIG. 9 shows that the transverse electrical field strength 17 is greatest adjacent the electrical modulation lead 12 and falls off lateral of the electrical modulation lead 12. This field strength 17 drop-off forms a sizable gradient in the transverse direction, which activates the neural cell terminals in the dorsal horn. The generated electrical field has an elongate, or stripe, shape with a tapering at either or both ends of the stripe to minimize stimulation of the dorsal column.

The stripe shape of the generated electrical field stimulates the dorsal horn across a large longitudinal span (i.e., along most or all of the lead 12), thereby eliminating the need for electrical field localization in neuromodulation. A subsequent step or series of steps could be used to reduce the span of dorsal horn stimulation to save energy. Also, the substantially constant longitudinal electrical field and the large gradient in the transverse electrical field favor stimulation of dorsal horn neuronal elements over dorsal column neuronal elements. This electrical field makes the dorsal column neuronal elements even less excitable relative to the dorsal horn neuronal elements.

FIG. 10 depicts two electrical modulation leads 12 have been implanted over the spinal cord 11 of the patient. One of the electrical modulation lead 12 has been implanted more laterally with respect to the spinal cord 11, thereby placing it proximate the dorsal horn 13 of the spinal cord 11. The other electrical modulation lead 12 has been implanted more medially with respect to the spinal cord 11, thereby placing it proximate the dorsal column of the spinal cord 11. Use of the SCM system to fractionalize the current to the electrical modulation leads 12 and the case 44 of the IPG 14 is depicted in FIG. 5. While FIG. 10 depicts two electrical modulation leads 12, any other plurality of leads 12 or a multiple column paddle lead can also be used with the disclosed method.

As shown FIG. 5, the manual programming mode has been selected. In the manual programming mode, each of the electrodes 130 of the graphical leads 128, as well as the graphical case 132, may be individually selected, allowing the clinician to set the polarity (cathode or anode) and the magnitude of the current (percentage) allocated to that electrode 130, 132 using graphical controls located in an amplitude/polarity area 144 of the parameter adjustment panel 106. Electrode E15 is shown as being selected to allow the user to subsequently allocate the polarity and fractionalized electrical current to it via the graphical controls located in the amplitude/polarity area 144.

In particular, a graphical polarity control 146 located in the amplitude/polarity area 144 includes a "+" icon, a "−" icon, and an "OFF" icon, which can be respectively actuated to toggle the selected electrode 130, 132 between a positive polarization (anode), a negative polarization (cathode), and an off-state. An amplitude control 148 in the amplitude/polarity area 144 includes an arrow that can be actuated to decrease the magnitude of the fractionalized current of the selected electrode 130, 132, and an arrow that can be actuated to increase the magnitude of the fractionalized current of the selected electrode 130, 132. The amplitude control 148 also includes a display area that indicates the adjusted magnitude of the fractionalized current for the selected electrode 134. The amplitude control 148 is preferably disabled if no electrode is visible and selected in the lead display panel 104. In response to the adjustment of fractionalized electrode combination via manipulation of the graphical controls in the amplitude/polarity area 144, the controller/processor 80 generates a corresponding modulation parameter set (with a new fractionalized electrode combination) and transmits it to the IPG 14 via the telemetry circuitry 86 for use in delivering the modulation energy to the electrodes 26.

In the embodiment illustrated in FIG. 5, the graphical case 132 representing the case 44 of the IPG 14 has been selected as the cathode to which 100% of the cathodic current has been allocated, and electrodes E1 to E8 have each been selected as an anode to which 12.5% of the anodic current has been allocated. Accordingly, 100% of the anodic current has been distributed evenly across electrodes E1 to E8. Electrodes E1 to E8 correspond to electrodes 26 on the electrical modulation lead 12 implanted adjacent the dorsal horn 13. This embodiment approximates an electrical field with a small longitudinal gradient by making the broad assumption that the tissue over which each of electrodes E1 to E8 response similarly to electrical modulation energy delivered through the respective electrodes. Under this broad assumption, the electrical field generated by the electrical modulation energy delivered to the electrodes 130, 132 has a very small gradient in the longitudinal direction along the axis of the electrical modulation lead 12 represented by the graphical lead 128 on which electrodes E1 to E8 are displayed. The small gradient in the longitudinal direction avoids activation of the myelinated axons in the dorsal column. On the other hand, the electrical field has a sizable gradient in the transverse direction, which can activate the neural cell terminals in the dorsal horn.

Although the graphical controls located in the amplitude/polarity area 144 can be manipulated for any of the electrodes, a dedicated graphical control for selecting the polarity and fractionalized current value can be associated with each of the electrodes, as described in U.S. Patent Publication No. 2012/0290041, entitled "Neurostimulation System with On-Effector Programmer Control," which is expressly incorporated herein by reference.

The parameters adjustment panel 106, when the manual programming mode is selected, also includes an equalization control 150 that can be actuated to automatically equalize current allocation to all electrodes of a polarity selected by respective "Anode +" and "Cathode −" icons. The ranges of pulse rates and pulse widths of the modulation parameter sets defined during the manual programming can result in either super-threshold therapy and sub-threshold therapy. For example, the lower limit of the pulse amplitude may be as low as 0.1 mA, wherein as the upper limit of the pulse amplitude may be as high as 20 mA. The lower limit of the pulse width may be as low as 2 µs, whereas the upper limit of the pulse width may be as high as 1000 µs. For example, the lower limit of the pulse rate may be as low as 1 Hz, whereas the upper limit of the pulse rate may be as high as 50 KHz. In the illustrated embodiment, a pulse amplitude of 5 mA, a pulse width of 210 µs, and a pulse rate of 40 Hz have been selected. Thus, during the manual programming mode, the selected coverage area 120 of the selected program 114 can be programmed with a modulation parameter set designed to either deliver super-threshold therapy or sub-threshold therapy to the patient.

Figure 11:
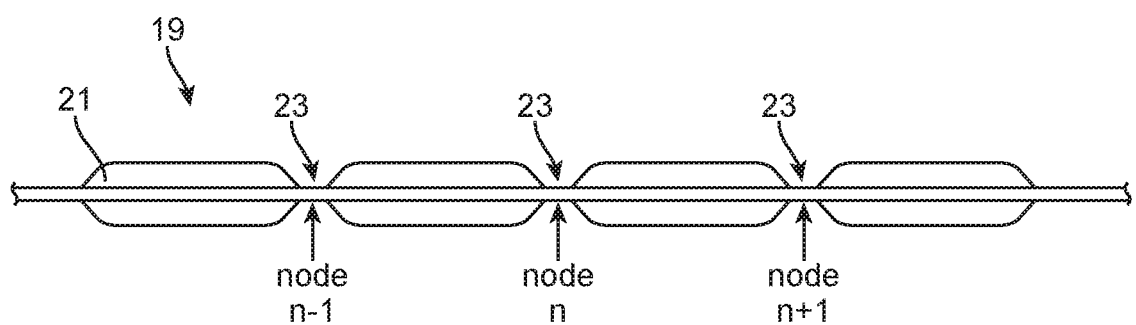
FIG. 11 is a schematic view of a myelinated axon in a dorsal column of a spinal cord.

Another embodiment of a method of programming an SCM system 10 includes modifying the fractionalized current delivered to each electrode 26 to minimize the electrical field gradient in the longitudinal direction, so as to minimize activation of the dorsal column neuronal elements. Minimizing activation of the dorsal or neuronal elements can include a model-based calculation, where the model includes the information from the manual or auto-calibration (described below). As shown in FIG. 11, the myelinated large axons 19 in the dorsal column have gaps in the myelination 21 that formed nodes 23. The anatomy depicted in FIG. 11 implies that the driving force for the myelinated large axons 19 generated by current delivered to an electrode 26 can be approximated with an activating function.

The discrete activating function can be calculated by the formula: $AF(n) = G_a/(\pi \times d \times l) \times [V_e(n-1) - 2\,V_e(n) + V_e(n+1)]$, wherein $G_a$ is the axonal intermodal conductance, d is the axonal diameter, l is the length of the node of Ranvier, $V_e(n)$ is the strength of the electric field at the node for which the activating function is determined, $V_e(n-1)$ is the strength of the electric field at the node preceding the node 23 for which the activating function is determined, and $V_e(n+1)$ is the strength of the electric field at the node 23 following the node 23 for which the activating function is determined. Using this formula, the discrete activating function is calculated from the conductance normalize to the surface area of the node of Ranvier.

The perception threshold is the modulation signal level above which a patient feels paresthesia. Because the perception threshold varies from patient to patient and from electrode 26 to electrode 26 within a patient, a more accurate fractionalization of the current between electrodes 26 requires modification of the fractionalization based on the perception threshold at each electrode. The perception threshold can be determined using the SCM system as described below.

A user (e.g., patient or clinician) can place the IPG 14 into Perception Threshold Identification Mode using the RC 16 or the CP 18, respectively. Once Perception Threshold Identification Mode is initiated, the IPG 14 is directed to sequentially deliver modulation energy to each of the electrodes 26 on a lead 12 at incrementally increasing modulation signals.

The IPG 14 may be configured for automatically incrementally increasing the modulation signal parameters of the electrical pulse train without further user intervention or may be configured for incrementally increasing the modulation signal parameters of the electrical pulse train delivered by the IPG 14 each time the user actuates a control element on the RC 16 or the CP 18.

The RC 16 or the CP 18 is configured for prompting the patient to actuate a control element, once paresthesia is perceived by the patient. In response to this user input, the RC 16 or the CP is configured to store the modulation signal strength of the electrical pulse train delivered when the control element is actuated. This modulation signal strength is identified as the perception threshold for the particular electrode 26.

Alternatively, rather than relying on voluntary user input, the RC 16 or the CP 18 may be configured for automatically identifying the perception threshold in response to a sensed physiological parameter indicative of super-threshold stimulation of the neural tissue (e.g., action potentials sensed by the IPG 14 at one or more electrodes 26 as a result of the delivery of the modulation energy ("local field potentials")). The above-described method for identifying a perception threshold may be repeated to identify the perception threshold at each of the electrodes 26 on a lead 12.

The identified perception thresholds can be used to estimate the current fractionalization by minimizing the sum of the square of the discrete activating function divided by the determined perception threshold at each electrode 26 on an electrical modulation lead 12. Squaring the discrete activating function, or any driving force from the electrical field, eliminates the differences in depolarizing and hyperpolarizing fields. The current fractionalization that results in a minimize sum minimizes the field gradient in the longitudinal direction.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A non-transitory machine-readable medium including instructions, which when executed by a machine, cause the machine to deliver an electrical waveform from an implantable neuromodulator to at least some electrodes in an electrode array in accordance with a modulation parameter set to generate an electric field to stimulate dorsal horn neuronal elements more than dorsal column neuronal elements, wherein:
   a first component of the electrical field generated using the electrical waveform extends along a spinal cord of the patient and a second component of the electrical field generated using the electrical waveform extends transverse to the spinal cord of the patient; and
   a gradient across the first component of the electrical field renders the dorsal column neuronal elements less excitable than the dorsal horn neuronal elements are rendered by a gradient across the second component of the electrical field.

2. The non-transitory machine-readable medium of claim 1, wherein the electrical waveform delivered in accordance with the modulation parameter set parameter set is configured to generate a first driving force in dorsal horn neuronal elements that is stronger than a second driving force in dorsal column neuronal elements.

3. The non-transitory machine-readable medium of claim 1, wherein the modulation parameter set defines an electrode combination, wherein the electrode combination comprises a fractionalized electrode combination.

4. The non-transitory machine-readable medium of claim 3, wherein the fractionalized electrode combination is configured such that all electrodes on an electrical modulation lead have the same polarity.

5. The non-transitory machine-readable medium of claim 1, wherein the electrical field has an elongated shape disposed over a dorsal horn of a spinal cord of the patient, and the elongated shape has a longitudinal axis parallel to the spinal cord of the patient.

6. The non-transitory machine-readable medium of claim 1, wherein the generated electric field does not cause the patient to perceive paresthesia.

7. The non-transitory machine-readable medium of claim 1, wherein the instructions, which when executed by a machine, cause the machine to:
   determine a perception threshold for electrical modulation energy conveyed through each electrode of a plurality of electrodes on an electrical modulation lead;
   modify a neuronal driving force indicator for electrical modulation energy conveyed through each electrode of the plurality based on the respective determined perception threshold; and
   modify the modulation parameter set based on the modified neuronal driving force indicator for electrical modulation energy conveyed through each electrode of the plurality before delivering the electrical waveform in accordance with the modulation parameter set.

8. The non-transitory machine-readable medium of claim 7, wherein the neuronal driving force indicator is an activating function.

9. The non-transitory machine-readable medium of claim 7, wherein the perception threshold is determined using patient feedback.

10. The non-transitory machine-readable medium of claim 7, wherein the perception threshold is determined by measuring local field potentials.

11. A system for use with an implantable electrode array, the system comprising:
   an implantable neuromodulator configured to be coupled to the implantable electrode array, the implantable neuromodulator including a modulation output circuitry to generate an electrical waveform and a control circuitry configured to cooperate with the modulation output circuitry to deliver the electrical waveform to at least some electrodes in the electrode array in accordance with a modulation parameter set to generate an electric field to stimulate dorsal horn neuronal elements more than dorsal column neuronal element, wherein:
   a first component of the electrical field generated using the electrical waveform extends along a spinal cord of the patient and a second component of the electrical field generated using the electrical waveform extends transverse to the spinal cord of the patient; and
   a gradient across the first component of the electrical field renders the dorsal column neuronal elements less excitable than the dorsal horn neuronal elements are rendered by a gradient across the second component of the electrical field.

12. The system of claim 11, wherein the electrical waveform delivered in accordance with the modulation parameter set parameter set is configured to generate a first driving force in dorsal horn neuronal elements that is stronger than a second driving force in dorsal column neuronal elements.

13. The system of claim 11, wherein the modulation parameter set defines an electrode combination, wherein the electrode combination comprises a fractionalized electrode combination.

14. The system of claim 13, wherein the fractionalized electrode combination is configured such that all electrodes on an electrical modulation lead have the same polarity.

15. The system of claim 11, wherein the electrical field has an elongated shape disposed over a dorsal horn of a spinal cord of the patient, and the elongated shape has a longitudinal axis parallel to the spinal cord of the patient.

16. The system of claim 11, wherein the control circuitry configured to cooperate with the modulation output circuitry to:
determine a perception threshold for electrical modulation energy conveyed through each electrode of a plurality of electrodes on an electrical modulation lead;
modify a neuronal driving force indicator for electrical modulation energy conveyed through each electrode of the plurality based on the respective determined perception threshold; and
modify the modulation parameter set based on the modified neuronal driving force indicator for electrical modulation energy conveyed through each electrode of the plurality before delivering the electrical waveform in accordance with the modulation parameter set.

17. The system of claim 16, wherein the neuronal driving force indicator is an activating function.

18. The system of claim 16, wherein the perception threshold is determined using patient feedback.

19. The system of claim 16, wherein the perception threshold is determined by measuring local field potentials at an electrode of the plurality of electrodes.

20. A method of operating an implantable neuromodulator coupled to an implanted electrode array, comprising:
delivering an electrical waveform from the implantable neuromodulator to at least some electrodes in the implanted electrode array in accordance with a modulation parameter set to generate an electric field, wherein:
a first component of the electrical field generated using the electrical waveform extends along a spinal cord of the patient and a second component of the electrical field generated using the electrical waveform extends transverse to the spinal cord of the patient; and
a gradient across the first component of the electrical field is weaker than a gradient across the second component of the electrical field.

* * * * *